United States Patent
Hayashi et al.

(10) Patent No.: US 9,881,517 B2
(45) Date of Patent: Jan. 30, 2018

(54) INFORMATION PROCESSING DEVICE AND STORAGE MEDIUM

(71) Applicant: SONY CORPORATION, Tokyo (JP)

(72) Inventors: Kazunori Hayashi, Tokyo (JP); Yoichiro Sako, Tokyo (JP); Takayasu Kon, Tokyo (JP); Yasunori Kamada, Kanagawa (JP); Takatoshi Nakamura, Tokyo (JP); Hiroyuki Hanaya, Kanagawa (JP); Tomoya Onuma, Shizuoka (JP); Akira Tange, Tokyo (JP)

(73) Assignee: SONY CORPORATION, Tokyo (JP)

( * ) Notice: Subject to any disclaimer, the term of this patent is extended or adjusted under 35 U.S.C. 154(b) by 245 days.

(21) Appl. No.: 14/224,330

(22) Filed: Mar. 25, 2014

(65) Prior Publication Data
US 2014/0315160 A1 Oct. 23, 2014

(30) Foreign Application Priority Data
Apr. 18, 2013 (JP) ................................. 2013-087527

(51) Int. Cl.
G09B 19/00 (2006.01)
A47G 21/06 (2006.01)
G02B 27/01 (2006.01)
A47G 21/00 (2006.01)

(52) U.S. Cl.
CPC ....... *G09B 19/0092* (2013.01); *A47G 21/103* (2013.01); *G02B 27/017* (2013.01); *A47G 21/00* (2013.01); *A47G 2200/08* (2013.01); *A47G 2200/205* (2013.01); *G02B 2027/014* (2013.01)

(58) Field of Classification Search
CPC ...................................................... G09B 19/00
USPC ............................................................ 434/127
See application file for complete search history.

(56) References Cited

U.S. PATENT DOCUMENTS

| | | | |
|---|---|---|---|
| 6,336,136 B1 * | 1/2002 | Harris ................. | G06F 19/3475 128/921 |
| 6,508,762 B2 * | 1/2003 | Karnieli ................ | G06F 19/324 128/921 |
| 7,077,806 B2 * | 7/2006 | Ackermann .......... | G06Q 50/24 128/904 |
| 8,345,930 B2 * | 1/2013 | Tamrakar .............. | G06T 7/0002 382/110 |

(Continued)

FOREIGN PATENT DOCUMENTS

| | | |
|---|---|---|
| JP | 2002-048180 | 2/2002 |
| JP | 2007-048180 | 2/2007 |

OTHER PUBLICATIONS

Sep. 4, 2017, CN communication issued for related CN application No. 201410145431.7.

*Primary Examiner* — Sam Yao
*Assistant Examiner* — Alvin Carlos
(74) *Attorney, Agent, or Firm* — Paratus Law Group, PLLC

(57) ABSTRACT

There is provided an information processing device including a detection unit configured to detect a plurality of pieces of food which are eating targets from an image obtained by imaging eating of a user, and a recommendation unit configured to recommend at least the food to be subsequently ingested in real time among the plurality of pieces of food so that the user ingests the plurality of pieces of food detected by the detection unit in an order satisfying a predetermined purpose.

13 Claims, 8 Drawing Sheets

(56) References Cited

U.S. PATENT DOCUMENTS

| | | | | |
|---|---|---|---|---|
| 8,363,913 B2* | 1/2013 | Boushey | ................... | G06K 9/00 |
| | | | | 128/921 |
| 8,439,683 B2* | 5/2013 | Puri | ................... | G09B 19/0092 |
| | | | | 434/127 |
| 9,104,943 B2* | 8/2015 | Sato | ...................... | G06K 9/4642 |
| 9,165,398 B2* | 10/2015 | Kim | ....................... | G06Q 10/00 |
| 2002/0022774 A1* | 2/2002 | Karnieli | ................. | G06F 19/324 |
| | | | | 600/300 |
| 2003/0059747 A1* | 3/2003 | Yoshida | ................. | G06Q 10/10 |
| | | | | 434/127 |
| 2003/0076983 A1* | 4/2003 | Cox | .................... | G06F 19/3475 |
| | | | | 382/110 |
| 2006/0229504 A1* | 10/2006 | Johnson, Jr. | ......... | G06F 19/3475 |
| | | | | 600/300 |
| 2011/0318717 A1* | 12/2011 | Adamowicz | ....... | G09B 19/0092 |
| | | | | 434/127 |
| 2013/0335418 A1* | 12/2013 | Kim | ....................... | G06Q 10/00 |
| | | | | 345/424 |
| 2014/0081578 A1* | 3/2014 | Connor | ............... | G06F 19/3475 |
| | | | | 702/19 |

* cited by examiner

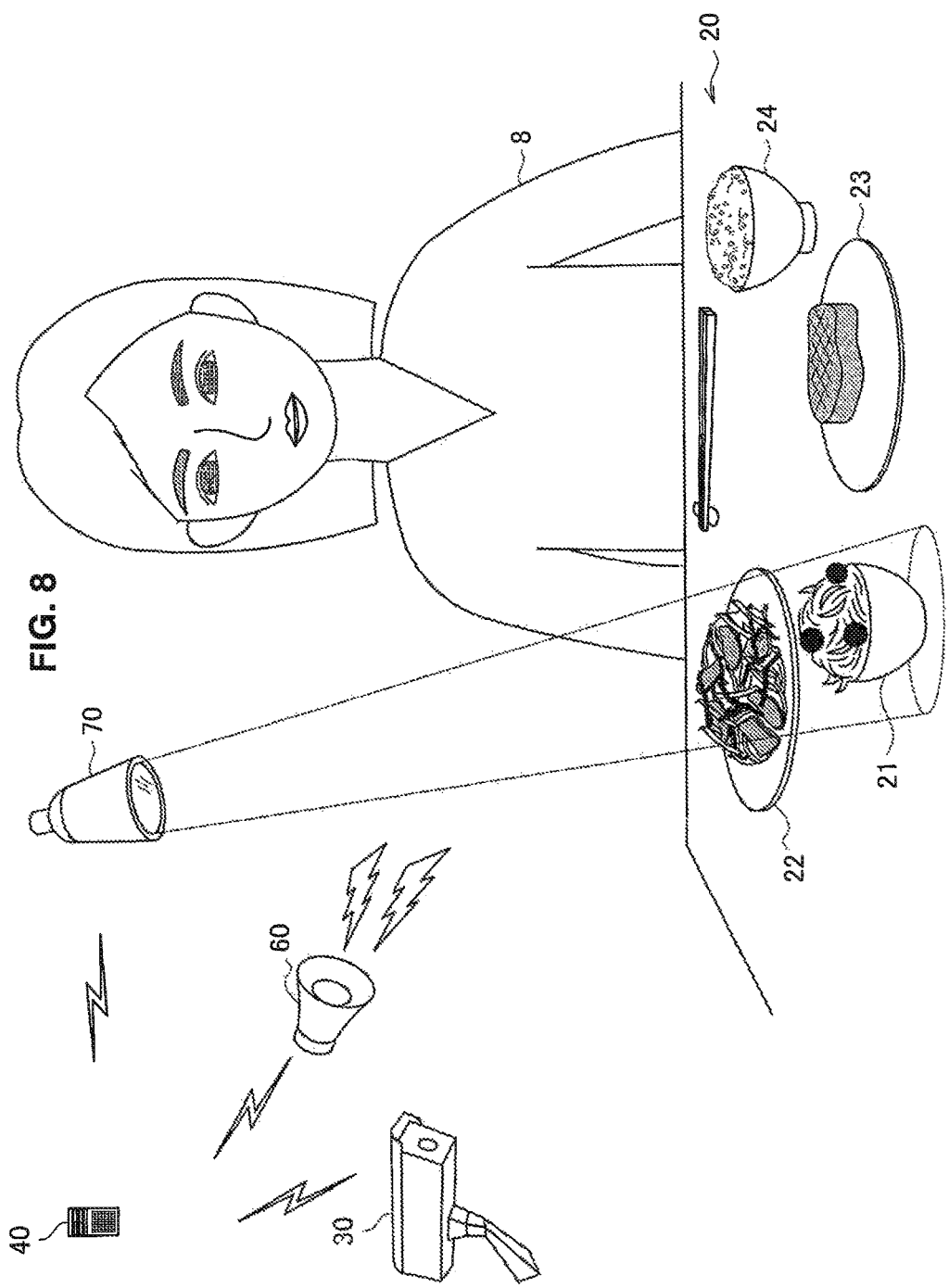

INFORMATION PROCESSING DEVICE AND STORAGE MEDIUM

CROSS REFERENCE TO RELATED APPLICATIONS

This application claims the benefit of Japanese Priority Patent Application JP 2013-087527 filed Apr. 18, 2013, the entire contents of which are incorporated herein by reference.

BACKGROUND

The present disclosure relates to an information processing device and a storage medium.

In recent years, as dietary life becomes rich, concerns that human health may be harmed due to various symptoms such as obesity, hyperlipemia, and hyperglycemia have increased. For this reason, various technologies for supporting dietary life have been developed to improve human health in the aspect of diet.

For example, JP 2007-48180A discloses a technology for monitoring a heart rate of a user during a meal in real time and performing navigating so that the user ingests a meal at an appropriate speed based on a change in the heart rate.

Also, JP 2002-149828A discloses a technology for transmitting captured images before a meal, during the meal, and after the meal to a mentor such as a dietitian or a doctor and receiving guidance regarding a nutritional balance or a menu from the mentor located at a remote location.

SUMMARY

In general, even for the same food (hereinafter, "food" can include drink), an absorption ratio of nutritional components is known to be changed according to an order of eating (hereinafter, "eating" can include drinking). However, JP 2007-48180A and JP2002-149828A have not mentioned any real-time navigation of an order of eating based on a change in an absorption ratio of nutritional components according to such an order of eating.

It is desirable to provide a novel and improved information processing device and a novel and improved storage medium capable of promoting health of a user by performing navigation regarding an order of eating in real time.

According to an embodiment of the present disclosure, there is provided an information processing device including a detection unit configured to detect a plurality of pieces of food which are eating targets from an image obtained by imaging eating of a user, and a recommendation unit configured to recommend at least the food to be subsequently ingested in real time among the plurality of pieces of food so that the user ingests the plurality of pieces of food detected by the detection unit in an order satisfying a predetermined purpose.

According to an embodiment of the present disclosure, there is provided a non-transitory computer-readable storage medium having a program stored therein, the program causing a computer to execute detecting a plurality of pieces of food which are eating targets from an image obtained by imaging eating of a user, and recommending at least the food to be subsequently ingested in real time among the plurality of pieces of food so that the user ingests the plurality of pieces of food detected by the user in an order satisfying a predetermined purpose.

According to embodiments of the present disclosure described above, it is possible to promote health of a user by performing navigation regarding an order of eating in real time.

BRIEF DESCRIPTION OF THE DRAWINGS

FIG. 8 is an explanatory diagram illustrating an overview of a recommendation system according to a modification example.

DETAILED DESCRIPTION OF THE EMBODIMENTS

Figure 1:
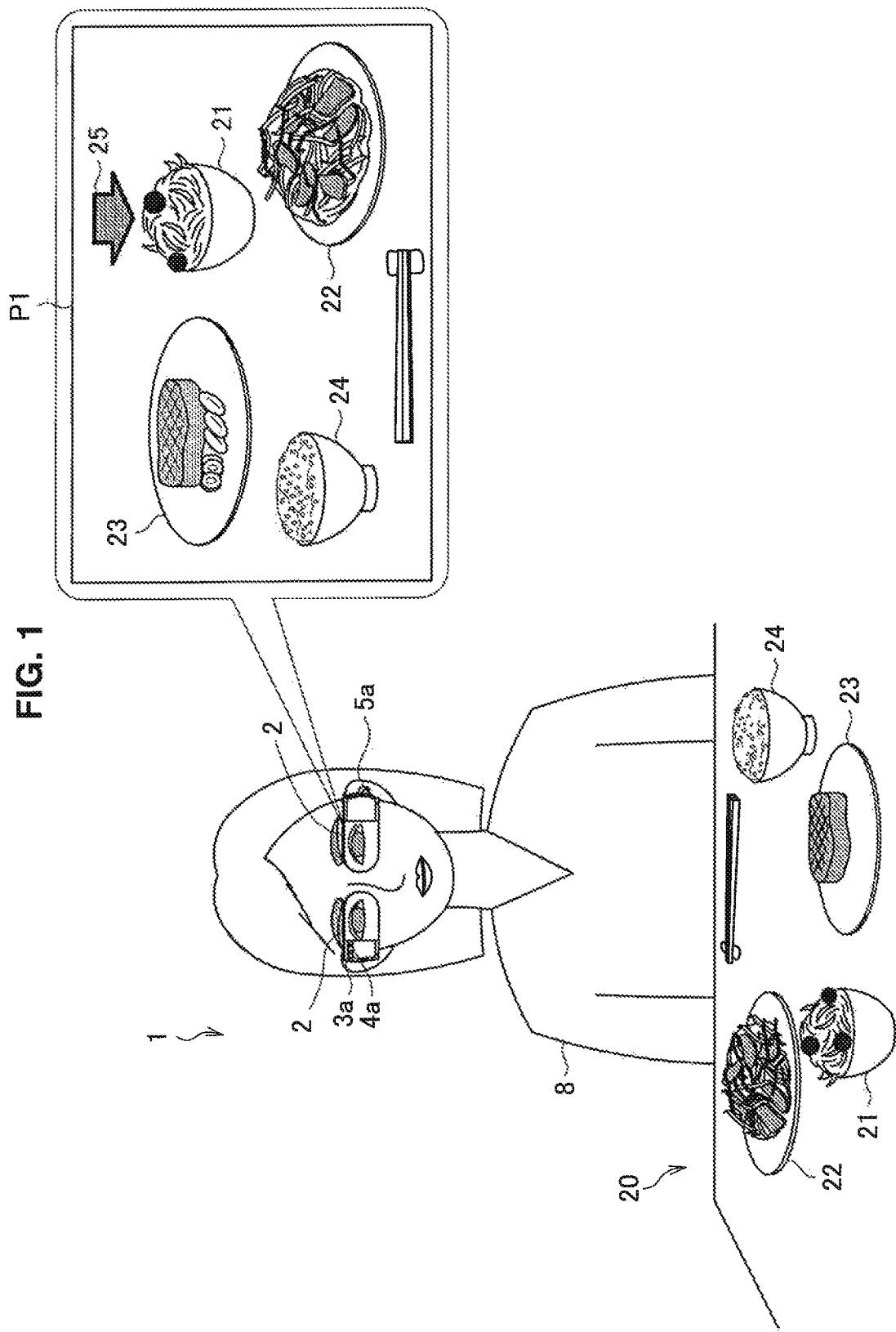
FIG. 1 is an explanatory diagram illustrating an overview of a recommendation process according to an embodiment of the present disclosure.

Hereinafter, preferred embodiments of the present disclosure will be described in detail with reference to the appended drawings. Note that, in this specification and the appended drawings, the same reference numerals are given to constituent elements having substantially the same functional configuration and repeated description thereof will be omitted.

The description will be made in the following order.
1. Overview of recommendation process according to embodiment of the present disclosure
2. Embodiments
2-1. First embodiment
2-1-1. Configuration of HMD
2-1-2. Operational process of HMD
2-2. Second embodiment
2-2-1. Overview of recommendation system
2-2-2. Configuration of recommendation system
2-2-3. Operational process of recommendation system
2-2-4. Modification example
3. Conclusion

1. OVERVIEW OF RECOMMENDATION PROCESS ACCORDING TO EMBODIMENT OF THE PRESENT DISCLOSURE

First, an overview of a recommendation process according to an embodiment of the present disclosure will be described with reference to FIG. 1.

FIG. 1 is an explanatory diagram illustrating the overview of the recommendation process according to the embodiment of the present disclosure. As illustrated in FIG. 1, a glasses-type head mounted display (HMD) 1 is mounted on a user 8. The HMD 1 includes a mounting unit which has, for example, a frame structure that extends in a semicircular shape from the both sides of the head to the back of the head and is suspended on both auricles, as illustrated in FIG. 1, to be mounted on the user 8.

Also, the HMD 1 is configured such that a pair of display units 2 for left and right eyes are disposed immediately before both eyes of the user 8 in the mounted state, that is, at positions at which the lenses of normal glasses are located. For example, a captured image of a real space imaged by an imaging lens 3a is displayed on the display units 2. Also, the display units 2 may be of a transmission type. Moreover, by causing the display units 2 to enter a through state, i.e., a transparent state or a semi-transparent state by the HMD 1, the user 8 does not experience trouble in normal life even when the HMD 1 is constantly mounted as in glasses.

Also, as illustrated in FIG. 1, the imaging lens 3a that performs imaging using a viewing direction of the user as a subject direction is disposed to be oriented forward in the HMD 1 when the HMD 1 is mounted on the user 8. Also, a light-emitting unit 4a that performs illumination in an imaging direction by the imaging lens 3a is installed. The light-emitting unit 4a is formed by, for example, a light-emitting diode (LED).

Also, although illustrated only on the left ear side in FIG. 1, a pair of earphone speakers 5a which can be inserted into right and left ear holes of the user in the mounted state are installed.

Also, the outer appearance of the HMD 1 illustrated in FIG. 1 is merely an example and diverse structures for mounting the HMD 1 on the user can be considered. The HMD 1 may be generally formed as a glasses type or head-mounted type mounted unit. In the present embodiment, the display units 2 may at least be installed closely in front of the eyes of the user. Also, not only may the pair of display units 2 be installed to correspond to both eyes, but the single display unit may also be installed to correspond to one eye.

Also, the imaging lens 3a and the light-emitting unit 4a performing illumination are disposed to be oriented forward on the side of the right eye in the example illustrated in FIG. 1, but may be disposed on the side of the left eye or may be disposed on both sides of the eyes.

Also, a single earphone speaker 5a may be installed so as to be mounted on only one ear rather than the left and right stereo speakers.

Further, the earphone speakers 5a may be configured not to be included. Also, the light-emitting unit 4a may be configured not to be included.

The outer appearance of the HMD 1 illustrated in FIG. 1 has been described above.

Here, as an example of a method of eating a healthy meal, imposing a meal restriction to suppress total calories ingested by, for example, a menu for reducing an amount of lipids or carbohydrates can be considered. However, since an absorption ratio of nutritional components is changed according to an order of eating, total calories absorbed by a human may not be said to be suppressed by merely suppressing total ingested calories. For example, when a user starts eating carbohydrates on an empty stomach, there is a probability of a blood-sugar level sharply increasing. Also, since the meal restriction causes the user to feel dissatisfied about not eating what he or she wants to eat and lowers pleasure of the meal, there are difficulties in continuously performing the meal restriction. In view of such a circumstance, convenience of a technology for supporting dietary life is considerably improved when navigation of a user's order of eating can be performed in real time.

Accordingly, in light of the above circumstance, a recommendation process according to each embodiment of the present disclosure has been created. The recommendation process according to each embodiment of the present disclosure is a process of performing navigation of an order of eating by recommending food to be subsequently ingested in real time.

Specifically, the HMD 1 (information processing device) illustrated in FIG. 1 causes the imaging lens 3a to image a plurality of dishes 20 placed on a table and detects the dishes 20 as food which are a plurality of eating targets from the captured image. In the example illustrated in FIG. 1, the HMD 1 detects a salad 21, fried liver and chives 22, a meat dish 23, and cooked rice 24 as the dishes 20 which are eating targets. Then, the HMD 1 can perform the navigation of the order of eating for the user 8 by displaying the dishes 20 to be subsequently ingested on the display units 2 so that the user 8 ingests the dishes 20 in an order satisfying a predetermined purpose.

The order satisfying the predetermined purpose can be considered diversely. Here, for example, suppression of an increase in a blood-sugar level of the user 8 can be considered. As described above, when the user starts eating carbohydrates on an empty stomach, there is a probability of a blood-sugar level sharply increasing. Therefore, the HMD 1 recommends that the user 8 ingest carbohydrates after ingesting vegetables.

As an example of the recommendation process performed by the HMD 1, for example, as illustrated in FIG. 1, the display units 2 display an image P1 in which the dish 20 to be subsequently ingested is displayed in an emphatic manner. The HMD 1 displays a navigation image 25 indicating the salad 21 so that the user first ingests the salad 21 containing many vegetables under the assumption that the user first ingests vegetables for the purpose of suppressing the increase in the blood-sugar level. At this time, the HMD 1 may display the navigation image 25 on the captured image in an overlapping manner or may display the navigation image 25 to correspond to the salad 21 present in the real space after controlling the display units 2 such that a semi-transmission type is set.

The overview of the recommendation process according to the present embodiment has been described above. Next, a configuration and an operational process of the HMD 1 (information processing device) performing the recommendation process according to an embodiment of the present disclosure will be described with reference to FIGS. 2 to 4.

2. EMBODIMENTS

2-1. First Embodiment

2-1-1. Configuration of HMD

Figure 2:
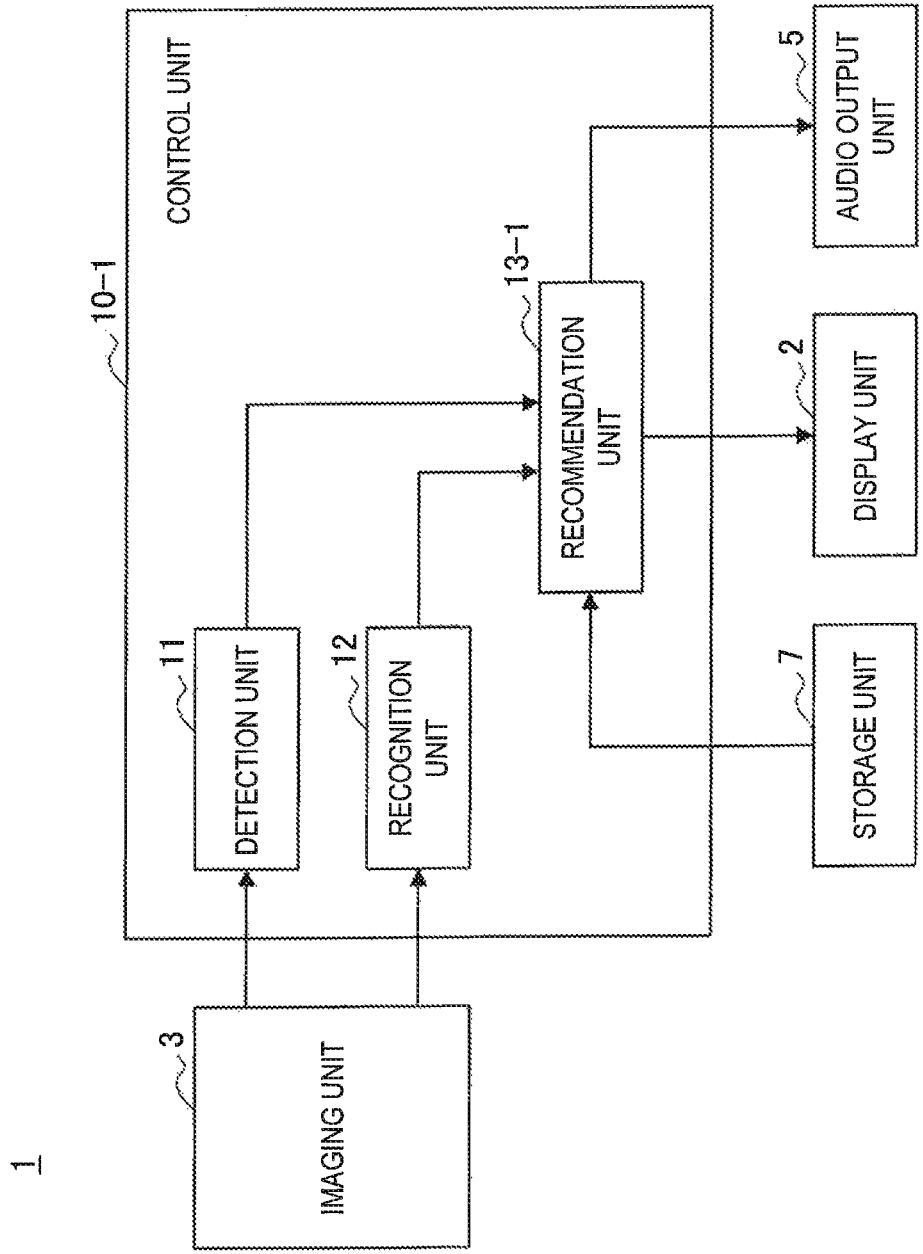
FIG. 2 is a block diagram illustrating an internal configuration of an HMD according to a first embodiment.

FIG. 2 is a block diagram illustrating an internal configuration of an HMD 1 according to a first embodiment. As illustrated in FIG. 2, the HMD 1 according to the present embodiment includes a display unit 2, an imaging unit 3, an audio output unit 5, a storage unit 7, and a control unit 10-1. Also, in FIG. 2, the configuration illustrated in FIG. 1 is partially omitted.

(Imaging Unit 3)

The imaging unit 3 includes a lens system that includes the imaging lens 3a, a diaphragm, a zoom lens, and a focus lens, a driving system that performs a focus operation or a zoom operation on the lens system, and a solid-state image sensor array that photoelectrically converts imaging light obtainable from the lens system and generates an imaging signal. The solid-state image sensor array may be realized by, for example, a charge coupled device (CCD) sensor array or a complementary metal oxide semiconductor (CMOS) sensor array. The imaging unit 3 outputs data regarding a photographed image considered as a digital signal.

Also, the imaging unit 3 may further include an illumination unit 4 that includes the light-emitting unit 4a illustrated in FIG. 1 and a light-emitting circuit causing the light-emitting unit 4a (for example, an LED) to emit light. In addition, upon capturing an image, the imaging unit 3 may perform imaging after illumination of a visual field direction of the user 8 by causing the illumination unit 4 to emit light forward.

The imaging unit 3 images the dishes 20 which are eating targets of the user 8 or eating of the user 8 such as eating actions of the user 8, and then outputs the captured image.

(Storage Unit 7)

The storage unit 7 has a function of an accumulation unit that accumulates a history of the past eating of the user 8. For example, when the storage unit 7 accumulates a history of eating for the past year of the user 8, the control unit 10-1 can recognize an eating tendency of the user 8, such as a favorite food of the user 8 or an order of eating, the number of chews, and a time taken for a meal. Furthermore, when the storage unit 7 accumulates a history of the eating for the past week of the user 8, the control unit 10-1 can recognize currently insufficient nutrients of the user 8.

(Control Unit 10-1)

The control unit 10-1 functions as an arithmetic processing device and a control device and controls all of the operations in the HMD 1 according to various programs. The control unit 10-1 is realized by, for example, a central processing unit (CPU) or a microprocessor. Also, the control unit 10-1 may include a read-only memory (ROM) that stores a program or an arithmetic parameter to be used and a random access memory (RAM) that temporarily stores a parameter which appropriately changes.

Specifically, the control unit 10-1 selects the food to be subsequently ingested by the user 8 based on the captured image output by the imaging unit 3 and recommends the selected food to the user 8 through at least one of the display unit 2 and the audio output unit 5. The control unit 10-1 functions as a detection unit 11, a recognition unit 12, and a recommendation unit 13-1.

(Detection Unit 11)

The detection unit 11 has a function of detecting a plurality of pieces of food which are eating targets from the image obtained by imaging the eating of the user 8. For example, in the example illustrated in FIG. 1, the detection unit 11 detects the salad 21, the fried liver and chives 22, the meat dish 23, and the cooked rice 24 as a plurality of pieces of food which are eating targets of the user 8. The detection unit 11 outputs a detection result to the recommendation unit 13-1.

(Recognition Unit 12)

The recognition unit 12 has a function of recognizing an eating situation of the user 8 from the image obtained by imaging the eating of the user 8. Examples of the situations of the food include eating actions of the user 8 and the appearances of the plurality of pieces of food which are the eating targets of the user 8. For example, in the example illustrated in FIG. 1, the recognition unit 12 recognizes that the user 8 is now going to start eating based on the image captured by the imaging unit 3. Thereafter, when the user 8 ingests the salad 21, the recognition unit 12 recognizes that the user 8 ingests the salad 21 or that the amount of salad 21 is reduced due to the ingestion of the user 8. Also, the recognition unit 12 recognizes whether the user 8 ingests the food recommended by the recommendation unit 13-1 by an amount of food recommended by the recommendation unit 13-1. Furthermore, the recognition unit 12 may recognize positions such as the positions of the plurality of pieces of food which are the eating targets of the user 8, the positions of eating utensils such as chopsticks or a fork, and the positions of the hands of the user 8. The recognition unit 12 outputs the recognition result to the recommendation unit 13-1.

(Recommendation Unit 13-1)

The recommendation unit 13-1 has a function of recommending at least the food to be subsequently ingested among the plurality of pieces of food in real time so that the user 8 ingests the plurality of pieces of food detected by the detection unit 11 in an order satisfying a predetermined purpose. First, the recommendation unit 13-1 selects at least the food to be subsequently ingested among the plurality of pieces of food detected by the detection unit 11 in the order satisfying the predetermined purpose. A recommendation process performed by the recommendation unit 13-1 includes a selection process of selecting the food to be subsequently ingested and a recommendation display process of recommending and displaying the selected food. Hereinafter, the selection process and the recommendation display process will be described in sequence.

Selection Process

Diverse orders satisfying predetermined purposes can be considered. For example, an order set in the case of the purpose of diabetes countermeasures is an order of vinegar, a dairy product, vegetables, a protein substance such as meat or bean curd, and carbohydrates such as rice or bread, which is an order suppressing an increase in a blood-sugar level of the user 8. Also, an order set in the case of the purpose of obesity countermeasures is an order of vinegar, a dairy product, vegetables, a protein substance, and carbohydrates, which is an order suppressing an increase in a blood-sugar level of the user 8. Also, an order set in the case of the purpose of baby education is an order of "triangular eating" which is an order of a well balanced meal. Also, an order set in the case of the purpose of enjoyment is considered to be an order of ingesting milk before drinking alcohol and ingesting noodles after drinking alcohol. Furthermore, an order set in the case of the purpose of a comfortable meal is considered to be an order of ingesting other food until the temperature of frozen food or hot food becomes an appropriate temperature. Also, an order set in the case of the purpose of obeying guidance of a doctor is an order based on the guidance of the doctor.

For example, in the example illustrated in FIG. 1, when the purpose of diabetes countermeasures is set, the recommendation unit 13-1 selects the salad 21 containing many vegetables as food to be first ingested. Then, the recommendation unit 13-1 recommends the food to be subsequently ingested among the pieces of food in real time to the user 8 who is eating by outputting the selected food from at least one of the display unit 2 and the audio output unit 5. For example, in the example illustrated in FIG. 1, the recommendation unit 13-1 recommends the salad 21 to the user 8 in real time by displaying the image P1 showing the navigation image 25 indicating the salad 21 on the display unit 2.

Based on a rule for determining the order according to such a purpose, the recommendation unit 13-1 recommends the food to be subsequently ingested among the plurality of pieces of food detected by the detection unit 11. For example, a rule set in the case of the purpose of diabetes countermeasures regulates recommendation in the order of vinegar, a dairy product, vegetables, a protein substance, and carbohydrates. In the example illustrated in FIG. 1, the recommendation unit 13-1 recommends the salad 21 containing many vegetables based on this rule. Such a rule of the recommended order may be stored in the storage unit 7 or may be stored in a database (DB) of a server or the like (not illustrated) and the recommendation unit 13-1 may perform the recommendation appropriately with reference to the rule of the recommended order by a communication unit (not illustrated). Also, the rule may be set by the user 8 or may be automatically set by the HMD 1 according to a condition or the like of the user 8.

The recommendation unit 13-1 recommends at least the food to be subsequently ingested further based on the history accumulated by the storage unit 7. For example, based on the history of the past year accumulated by the storage unit 7, the recommendation unit 13-1 changes the recommended order according to the eating tendency of the user 8, such as a favorite food of the user 8 or an order of eating, the number of chews, and a time taken for a meal. Since the food is recommended to the user 8 in the order according to the preference of the user 8, the user 8 can ingest food naturally (without stress) in the order recommended by the recommendation unit 13-1. Furthermore, based on the history of the past week accumulated by the storage unit 7, the recommendation unit 13-1 may change the recommended order so that the user 8 can absorb more of nutrients that are currently insufficient for the user 8.

Also, the recommendation unit 13-1 recommends at least the food to be subsequently ingested further based on a situation recognized by the recognition unit 12. For example, the recommendation unit 13-1 recommends the food to be subsequently ingested to the user 8 based on a situation in which the user 8 has eaten the recommended food. Also, the recommendation unit 13-1 may decide an ingestion amount of recommended food. Then, when the recognition unit 12 recognizes that the user 8 has ingested the decided amount of food recommended by the recommendation unit 13-1, the recommendation unit 13-1 may recommend the food to be subsequently ingested to the user 8 again.

Furthermore, when the user 8 has not eaten the recommended food but has eaten another food, the recommendation unit 13-1 warns the user 8 or stops the recommendation. At this time, the recommendation unit 13-1 may select food to be recommended to the user 8 again. Also, when new food is added to the eating targets of the user 8, the recommendation unit 13-1 selects the food to be subsequently ingested again and recommends the selected food to the user 8. Also, when it is recognized that the user 8 is a child, the recommendation unit 13-1 changes the purpose to education and recommends food according to the "triangular eating," so that leftover food can be prevented.

The recommendation unit 13-1 may select at least the food to be subsequently ingested every time based on a situation recognized by the recognition unit 12 or may decide a preferable order of ingestion in advance and recommend the food to the user based on the order decided according to the situation. For example, in the example illustrated in FIG. 1, the recommendation unit 13-1 may first select the salad 21 to be ingested based on a situation that the user 8 is now going to start eating. Also, the recommendation unit 13-1 may decide the order in advance such that the salad 21 containing many vegetables is selected first, the fried liver and chives 22 containing next many vegetables is selected second, the meat dish 23 which is a protein substance is selected third, and the cooked rice 24 which is carbohydrates is selected fourth.

Recommendation Display Process

The recommendation unit 13-1 generates an emphasis image showing the food to be subsequently ingested in an emphatic manner and recommends the food to be subsequently ingested to the user 8 by causing the display unit 2 to display the emphasis image. Diverse types of emphasis images can be considered. For example, as illustrated in FIG. 1, the emphasis image may be the navigation image 25 indicating the salad 21 to be subsequently ingested. Furthermore, the emphasis image may be an image indicating the preferable order of ingestion for each food. For example, in the example illustrated in FIG. 1, the emphasis image may be an image in which an indication "first" is added to the salad 21, an indication "second" is added to the fried liver and chives 22, an indication "third" is added to the meat dish 23, and an indication "fourth" is added to the cooked rice 24. Also, the emphasis image may be an image surrounding the food to be subsequently ingested in a circular form or highlighting the food to be subsequently ingested. Here, other examples of the emphasis image generated by the recommendation unit 13-1 will be described with reference to FIG. 3.

Figure 3:
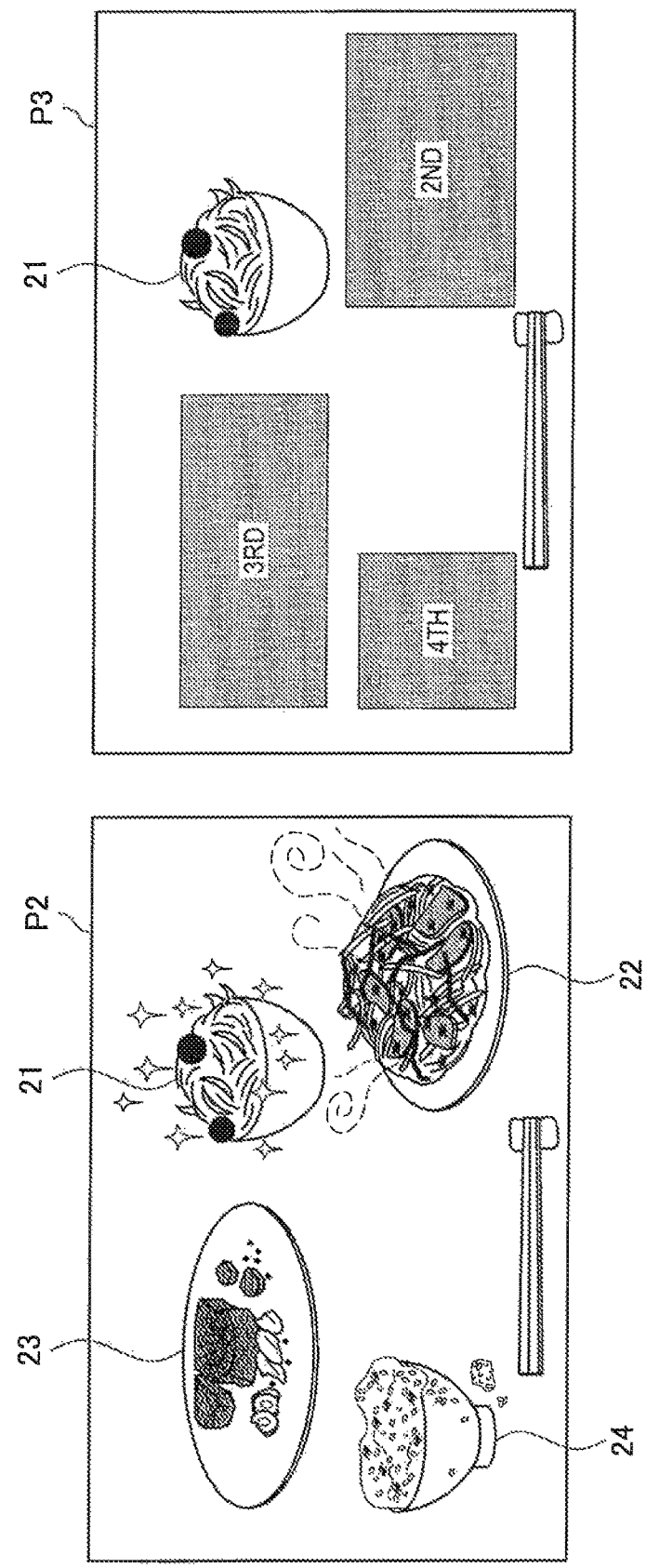
FIG. 3 is an explanatory diagram illustrating an example of an image displayed by the HMD according to the first embodiment.

FIG. 3 is an explanatory diagram illustrating examples of images displayed by the HMD 1 according to the first embodiment. As shown in an image P2 of FIG. 3, the emphasis image may be an image beautifying the outer appearance of the food to be subsequently ingested. The image P2 illustrated in FIG. 3 conveys an appetizing impression to the user 8 by causing the outer appearance of the salad 21 to be subsequently ingested to sparkle. Therefore, the user 8 first ingests the salad 21 that naturally looks appetizing. When the emphasis image beautifies the outer appearance of the food, the user 8 can ingest the food naturally in the order recommended by the recommendation unit 13-1 compared to the example in which the navigation image 25 illustrated in FIG. 1, the order, or the like is clearly displayed. Furthermore, the recommendation unit 13-1 may generate, as the emphasis image, an image in which a food material favored by the user 8 is added to food to be ingested or an image in which food is replaced with another food favored by the user 8.

Also, the recommendation unit 13-1 indirectly recommends the food to be subsequently ingested to the user 8 by generating an inhibitive image showing food to be inhibited from being subsequently ingested and causing the display unit 2 to display the inhibitive image. Diverse types of inhibitive images can be considered. For example, as shown in the image P2 of FIG. 3, the inhibitive image may be an image degrading the outer appearance of the food to be inhibited from being subsequently ingested. The image P2 illustrated in FIG. 3 gives an unpleasant-looking impression to the user 8 by causing the food other than the salad 21 to be subsequently ingested, i.e., the fried liver and chives 22 and the meat dish 23, to be inhibited from being subsequently ingested to look burnt and causing the cooked rice 24 to look unsanitary. Therefore, the user 8 avoids the fried liver and chives 22, the meat dish 23, and the cooked rice 24 which look naturally unappetizing and ingests the salad 21 first. When the inhibitive image is an image in which the outer appearance of the food is degraded, the food to be subsequently ingested can be recommended to the user 8 indirectly and naturally by causing the user 8 to naturally avoid the food to be inhibited from being subsequently ingested. Furthermore, the recommendation unit 13-1 may generate, as the inhibitive image, an image in which a food material disliked by the user 8 is added to food to be inhibited from being ingested or an image in which food is replaced with another food disliked by the user 8.

Furthermore, as shown in an image P3 of FIG. 3, the inhibitive image may be an image in which food to be inhibited from being subsequently ingested is screened from the user 8. In the image P3 illustrated in FIG. 3, the user 8 can recognize only the salad 21 because food other than the salad 21 to be subsequently ingested, i.e., the fried liver and chives 22, the meat dish 23, and the cooked rice 24 is grayed out to be inhibited from being subsequently ingested. Therefore, the user 8 can first ingest the recognizable salad 21.

Also, the recommendation unit 13-1 may recommend the preferable order of ingestion in units of food materials in the food. For example, in the example illustrated in FIG. 1, the recommendation unit 13-1 may recommend that the user ingest food in the order of bean sprouts, chives, and liver contained in the fried liver and chives 22.

(Display Unit 2)

The display unit 2 displays the captured image, or the emphasis image or the inhibitive image generated by the recommendation unit 13-1 under the control of the control unit 10-1.

Also, the display unit 2 according to the present embodiment displays the captured image in real time and further displays the emphasis image or the inhibitive image to correspond to the position of each item of food in the displayed captured image in an overlapping manner. Alternatively, after the display unit 2 is set to a through state (does not display the captured image), the display unit 2 may display the emphasis image or the inhibitive image to correspond to the position of the food present in the real space.

(Audio Output Unit 5)

The audio output unit 5 includes the pair of earphone speakers 5a illustrated in FIG. 1 and amplifier circuits corresponding to the earphone speakers 5a. Also, the audio output unit 5 may be formed as a so-called bone conduction speaker. The audio output unit 5 outputs (reproduces) audio signal data under the control of the control unit 10-1.

The internal configuration of the HMD 1 according to the present embodiment has been described above. Next, an operational process of the HMD 1 according to the present embodiment will be described.

2-1-2. Operational Process of HMD

The HMD 1 according to the present embodiment is mounted on the user 8, and recommends and displays at least the food to be subsequently ingested by the user 8 in real time during a meal of the user 8. Such a recommendation process performed by the HMD 1 will be described specifically with reference to FIG. 4.

Figure 4:
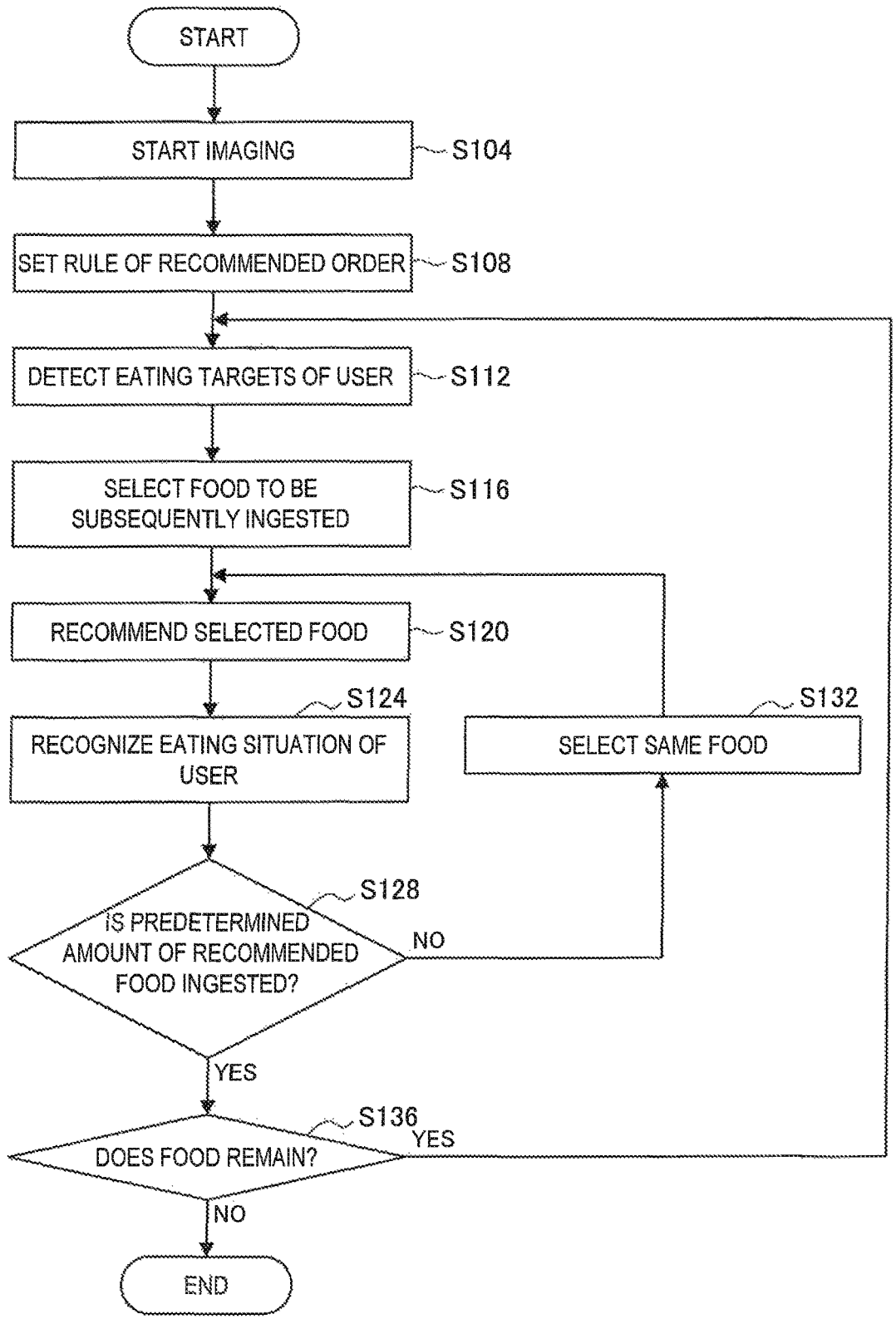
FIG. 4 is a flowchart illustrating a recommendation process of the HMD according to the first embodiment.

FIG. 4 is a flowchart illustrating the recommendation process of the HMD 1 according to the first embodiment. As illustrated in FIG. 4, the imaging unit 3 of the HMD 1 first starts imaging food in step S104.

Next, in step S108, the recommendation unit 13-1 sets a rule of a recommended order. For example, the recommendation unit 13-1 sets a rule of suppressing an increase in a blood-sugar level for the purpose of diabetes countermeasures based on the history of the past dietary life of the user 8 accumulated in the storage unit 7.

Subsequently, in step S112, the detection unit 11 detects a plurality of pieces of food which are eating targets of the user 8 from the image captured by the imaging unit 3. For example, in the example illustrated in FIG. 1, the detection unit 11 detects the salad 21, the fried liver and chives 22, the meat dish 23, and the cooked rice 24.

Next, in step S116, the recommendation unit 13-1 selects the food to be subsequently ingested. Specifically, the recommendation unit 13-1 selects the food to be subsequently ingested among the plurality of pieces of food detected by the detection unit 11 based on the rule of the recommended order, an eating situation recognized by the recognition unit 12, and the history of the eating accumulated in the storage unit 7. For example, in the example illustrated in FIG. 1, the recommendation unit 13-1 selects the salad 21 containing many vegetables as the food to be subsequently ingested based on the rule of suppressing an increase in the blood-sugar level and a situation that the user is now going to start eating.

Then, in step S120, the recommendation unit 13-1 recommends the selected food to the user 8. Specifically, the recommendation unit 13-1 generates at least one of an emphasis image emphasizing the selected food and an inhibitive image inhibiting the other unselected food and displays the generated image on the display unit 2. For example, as shown in the image P2 of FIG. 3, the recommendation unit 13-1 performs recommendation display such that the outer appearance of the selected salad 21 is beautified and the other food, i.e., the fried liver and chives 22, the meat dish 23, and the cooked rice 24, is degraded.

Subsequently, in step S124, the recognition unit 12 recognizes the eating situation of the user 8. Specifically, based on the image captured by the imaging unit 3, the recognition unit 12 recognizes whether the user 8 ingests the food recommended by the recommendation unit 13-1, and recognizes an eating action such as an eating speed or the number of chews or recognizes that the food ingested by the user 8 decreases. At this time, when the recognition unit 12 recognizes that the user 8 eats food other than the recommended food, the recommendation unit 13-1 performs the recommendation process again or a warning. When the user 8 does not follow the recommendation process or the warning, the recommendation process stops. Also, when the recognition unit 12 recognizes that new food is added as an eating target of the user 8, the recommendation unit 13-1 selects the food to be subsequently ingested again and recommends the selected food to the user 8 again.

Next, in step S128, the recognition unit 12 determines whether the user 8 ingests a predetermined amount of food recommended by the recommendation unit 13-1. Specifically, the recognition unit 12 determines whether the user 8 ingests the food recommended by the recommendation unit 13-1 by an amount decided by the recommendation unit 13-1.

When the user 8 does not ingest the predetermined amount of food recommended by the recommendation unit 13-1 (NO in S128), the recommendation unit 13-1 selects the same food in step S132 and the process returns to step S120 again. Thus, the recommendation unit 13-1 continues to recommend the same food until the user 8 ingests the decided amount of recommended food.

Conversely, when the user 8 ingests the predetermined amount of food recommended by the recommendation unit 13-1 (YES in S128), the recognition unit 12 determines whether the food remains in step S136. Specifically, based on the image captured by the imaging unit 3, the recognition unit 12 recognizes whether the food which is the eating target of the user 8 remains.

When the food remains (YES in S136), the process returns to step S112 again and the HMD 1 continuously performs the recommendation process for the user 8.

Conversely, when the food does not remain (NO in S136), the recommendation process ends.

The operational process of the HMD 1 according to the present embodiment has been described above.

(Supplement)

The HMD 1 may not only display food to be ingested and food to be inhibited from being ingested so that the user 8 can identify the food, but the HMD 1 may also perform display containing game components. As examples, when the user 8 eats the food in the recommended order, a high score can be given, or two recommendations can be presented and one of the two recommendations set as a correct answer. Thus, the user 8 can enjoy eating the food in the recommended order.

Also, in the present embodiment, the example in which the HMD 1 recommends food to the user 8 visually through image display has been described, but embodiments of the present disclosure are not limited to this example. For example, when the HMD 1 recommends food disliked by the user 8, the recommendation process may be performed by blocking a smell by pinching the nose of the user 8 or providing the user 8 with a smell of another food favored by the user 8. Thus, even when the user 8 dislikes food good for his or her health, the HMD 1 can support the user 8 such that the user 8 can eat the food in the recommended order without avoiding the food.

Also, in the present embodiment, the HMD 1 has been described as an example of an information processing device, but embodiments of the present disclosure are not limited thereto. Examples of the information processing device include a glasses-type display, a digital camera, a digital video camera, a Personal Digital Assistants (PDA), a Personal Computer (PC), a notebook-type PC, a tablet terminal, a smartphone, a portable telephone terminal, a portable music reproduction device, a portable video processing device, and a portable game device.

Also, in the present embodiment, the fact that the control unit 10-1 of the HMD 1 performs the recommendation process based on the captured image has been described, but the recommendation process may be performed on a cloud. For example, in the HMD 1, an image captured by the imaging unit 3 is transmitted via a communication unit (not illustrated) on a cloud, the food to be subsequently ingested may be selected based on the image on the cloud, a generated emphasis image and an inhibitive image may be received, and the display unit 2 may perform recommendation display based on the emphasis image and the inhibitive image. Also, the HMD 1 may have some of the functions of the detection unit 11, the recognition unit 12, the recommendation unit 13-1, and the storage unit 7 and the side of the cloud may have the other functions.

2-2. Second Embodiment

The present embodiment is an embodiment in which the food to be subsequently ingested is recommended and a user 8 is guided by an eating utensil gripped by the user 8. First, an overview of a recommendation system according to the present embodiment will be described with reference to FIG. 5.

2-2-1. Overview of Recommendation System

Figure 5:
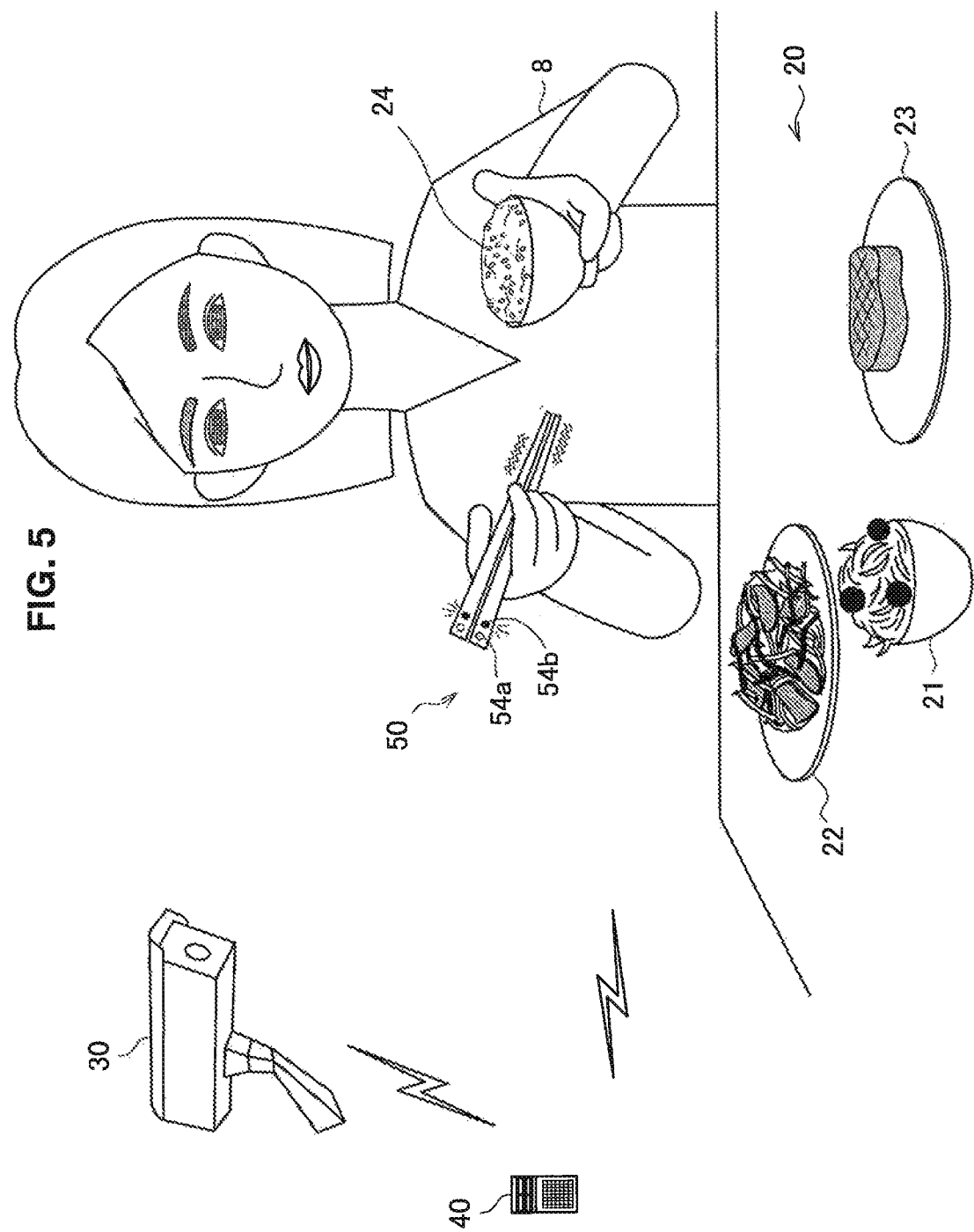
FIG. 5 is an explanatory diagram illustrating an overview of a recommendation system according to a second embodiment.

FIG. 5 is an explanatory diagram illustrating an overview of a recommendation system according to the second embodiment. As illustrated in FIG. 5, the recommendation system according to the present embodiment includes a camera 30, a server 40, and chopsticks 50 serving as an eating utensil. In the recommendation system according to the present embodiment, the camera 30 transmits an image obtained when the camera 30 images eating of the user 8 to the server 40, the server 40 selects the food to be subsequently ingested by the user 8, and the chopsticks 50 guide the user 8 to the food selected by the server 40.

The chopsticks 50 guide the user 8, for example, using a light-emitting unit 54a that emits green light and a light-emitting unit 54b that emits red light. For example, the food selected by the server 40 can be recommended and the user 8 can be guided in such a manner that the light-emitting unit 54a emits the green light when the user 8 approximates the chopsticks 50 to the food selected by the server 40 and the light-emitting unit 54b emits the red light when the user 8 approximates the chopsticks 50 to other food. Furthermore, the chopsticks 50 may guide the user 8 through vibration or gyroscopic moment. Also, in the present specification, the example in which the chopsticks 50 are used as the eating utensil has been described, but a knife, a fork, a spoon, or the like may be used as an eating utensil.

In the example illustrated in FIG. 5, the recommendation system controls the chopsticks 50 such that the user first ingests the salad 21 containing many vegetables under the assumption that the user first ingests vegetables for the purpose of diabetes countermeasures. More specifically, since the user 8 intends to ingest the cooked rice 24 rather than the recommended salad 21, the light-emitting unit 54b of the chopsticks 50 emits the red light and vibrates so that the user 8 can be notified that the user 8 is eating in a wrong order.

The overview of the recommendation system according to the present embodiment has been described above. Next, the configuration of the recommendation system according to the present embodiment will be described with reference to FIG. 6.

2-2-2. Configuration of Recommendation System

Figure 6:
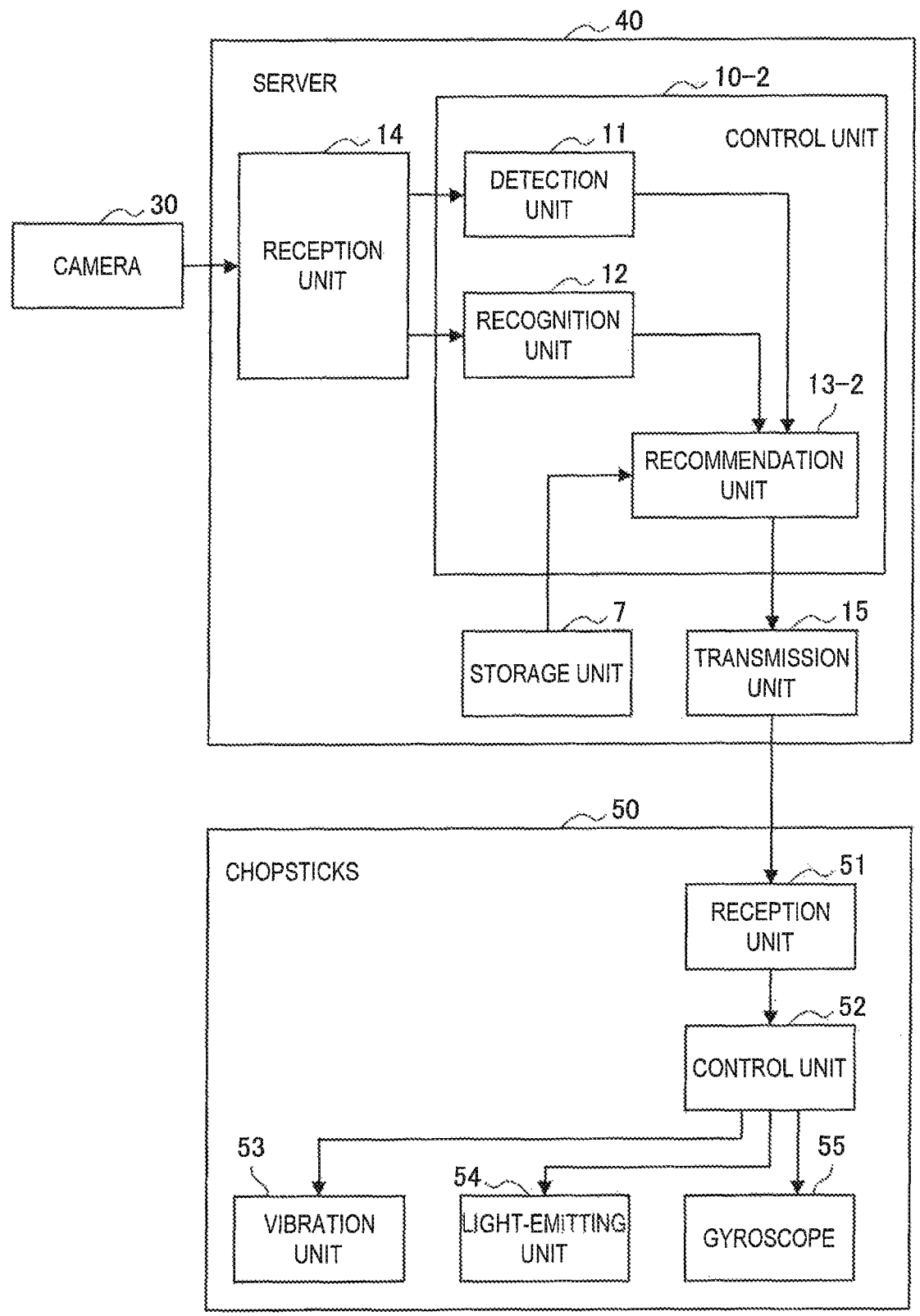
FIG. 6 is an explanatory diagram illustrating the configuration of the recommendation system according to the second embodiment.

FIG. 6 is an explanatory diagram illustrating the configuration of the recommendation system according to the second embodiment. As illustrated in FIG. 6, the recommendation system includes the camera 30, the server 40 (information processing device), and the chopsticks 50.

(Camera 30)

The camera 30 has the same function as the imaging unit 3 of the HMD 1 according to the foregoing first embodiment. That is, the camera 30 sets the entire table and the user 8 as an imaging range and images the dishes 20 which are eating targets of the user 8 or eating of the user 8 such as eating actions or the like of the user 8. Then, the camera 30 transmits a captured image to the server 40 in a wired or wireless manner.

(Server 40)

The server 40 has a function of recommending the food to be subsequently ingested to the user 8, as in the HMD 1 according to the foregoing first embodiment. Specifically, the server 40 selects the food to be subsequently ingested by the user 8 based on the captured image received from the camera 30. Then, the server 40 transmits, to the chopsticks 50, guidance information for guiding the user 8 to the selected food. The server 40 functions as a control unit 10-2, a storage unit 7, a reception unit 14, and a transmission unit 15. Also, since the storage unit 7 is the same as the storage unit described in the foregoing first embodiment, the detailed description thereof will be omitted here.

Reception Unit 14

The reception unit 14 is a communication module that transmits and receives data to and from the camera 30 in a wired or wireless manner. For example, the reception unit 14 performs communication with the camera 30 via a wireless local area network (LAN), a telephone line, or the like. In the present embodiment, the reception unit 14 receives an image obtained by imaging the eating of the user 8 from the camera 30 and outputs the image to the control unit 10-2.

Control Unit 10-2

The control unit 10-2 has the same function as the control unit 10-1 of the HMD 1 according to the foregoing first embodiment and includes a recommendation unit 13-2 instead of the recommendation unit 13-1. Since the detection unit 11 and the recognition unit 12 are the same as those described in the foregoing first embodiment, the detailed description thereof will be omitted here.

Recommendation Unit 13-2

The recommendation unit 13-2 performs the same selection process as the recommendation unit 13-1 of the HMD 1 according to the foregoing first embodiment. Thereafter, the recommendation unit 13-2 according to the present embodiment outputs guidance information for guiding the user 8 to ingest the selected (recommended) food. The guidance information includes information indicating whether the food to which the user 8 approximates the chopsticks 50 is the food recommended by the recommendation unit 13-2. For example, when the recognition unit 12 recognizes that the user 8 approximates the chopsticks 50 to the food to be subsequently ingested based on the image captured by the camera 30, the recommendation unit 13-2 outputs guidance information indicating that the user 8 is eating in the right order. On the other hand, when the recognition unit 12 recognizes that the user 8 approximates the chopsticks 50 to food to be inhibited from being subsequently ingested based on the image captured by the camera 30, the recommendation unit 13-2 outputs guidance information indicating that the user is eating in a wrong order. Furthermore, the guidance information may include positional information regarding each food recognized by the recognition unit 12, positional information regarding the selected food, and positional information regarding the chopsticks 50.

Transmission Unit 15

The transmission unit 15 is a communication module that wirelessly transmits and receives data to and from the chopsticks 50. For example, the transmission unit 15 performs communication with the chopsticks 50 via a wireless LAN or the like. In the present embodiment, the transmission unit 15 transmits, to the chopsticks 50, the guidance information for guiding the user to the food recommended by the recommendation unit 13-2. Also, when the user 8 exchanges the chopsticks 50 with another eating utensil, the transmission unit 15 may transmit the guidance information to the exchanged eating utensil so that the guidance can be continued by the exchanged eating utensil.

(Chopsticks 50)

The chopsticks 50 have a function of guiding the user 8 to the food recommended by the recommendation unit 13-2 based on the guidance information received from the server 40. The chopsticks 50 function as a reception unit 51, a control unit 52, a vibration unit 53, a light-emitting unit 54, and a gyroscope 55.

Reception Unit 51

The reception unit 51 is a communication module that wirelessly transmits and receives data to and from the server 40. For example, the reception unit 51 performs communication with the server 40 via a wireless LAN or the like. In the present embodiment, the reception unit 51 receives the guidance information transmitted from the server 40 and outputs the guidance information to the control unit 52.

Control Unit 52

The control unit 52 functions as an arithmetic processing device and a control device, and controls all of the operations in the chopsticks 50 according to various programs. The control unit 52 is realized by, for example, a CPU or a microprocessor. Also, the control unit 52 may include a ROM that stores a program, an arithmetic parameter, or the like to be used and a RAM that temporarily stores a parameter or the like which appropriately changes.

In the present embodiment, based on the guidance information received by the reception unit 51, the control unit 52 controls the vibration unit 53, the light-emitting unit 54, and the gyroscope 55 such that the user 8 is guided to the food recommended by the recommendation unit 13-2. More specifically, the control unit 52 controls the vibration unit 53, the light-emitting unit 54, and the gyroscope 55 based on information included in the guidance information and indicating whether the food to which the user 8 approximates the chopsticks 50 is the food recommended by the recommendation unit 13-2. Furthermore, based on various kinds of positional information included in the guidance information, the control unit 52 may determine whether the food to which the user 8 approximates the chopsticks 50 is the food recommended by the recommendation unit 13-2 and control the vibration unit 53, the light-emitting unit 54, and the gyroscope 55.

Vibration Unit 53

The vibration unit 53 vibrates the chopsticks 50 under the control of the control unit 52. That is, the vibration unit 53 has a vibration function of the chopsticks 50. The vibration unit 53 is realized by, for example, a vibration motor. In the present embodiment, for example, the vibration unit 53 guides the user 8 to the food selected by the recommendation unit 13-2 in such a manner that the vibration unit 53 does not vibrate when the user 8 approximates the chopsticks 50 to the food selected by the recommendation unit 13-2, and the vibration unit 53 vibrates when the user 8 approximates the chopsticks 50 to other food.

Light-Emitting Unit 54

The light-emitting unit 54 emits light under the control of the control unit 52. The light-emitting unit 54 is configured of, for example, the light-emitting units 54a and 54b illustrated in FIG. 5 which guide the user 8 to the food selected by the recommendation unit 13-2 by emitting light according to an operation of the user 8 approximating the chopsticks 50 to the food. For example, when the user 8 approximates the chopsticks 50 to the food selected by the recommendation unit 13-2, the light-emitting unit 54a emits the green light. When the user 8 approximates the chopsticks 50 to other food, the light-emitting unit 54b emits the red light. The light-emitting unit 54 is formed of, for example, an LED. Also, the light-emitting unit 54 may be one of the light-emitting units 54a and 54b.

Gyroscope 55

The gyroscope 55 has a function of guiding the user 8 gripping the chopsticks 50 in any direction by outputting a moment. The gyroscope 55 is realized by the technology disclosed in "Development of Non-grounded Force Display Using Gyro Moment Effect" by Masayuki Yoshie, Hiroaki Yano, and Hiroo Iwata, in the journal of the Virtual Reality Society of Japan Vol. 7 No. 3 (2002), for example. This document discloses the technology for presenting a sense of force by a gyroscope used for control or the like of an attitude of a satellite. More specifically, this technology is a technology for outputting a large moment to a small lightweight device using a moment produced when a rotation axis of a flywheel rotating at a high speed is tilted. In the present embodiment, the gyroscope 55 outputs a moment so that the chopsticks 50 are tilted in the direction of the food recommended by the chopsticks 50 based on various kinds of positional information included in the guidance information when the chopsticks 50 are gripped by the user 8 in the vertical direction. Thus, the user 8 can recognize that the food located in the direction in which the chopsticks 50 are tilted as the food to be subsequently ingested. Also, when the chopsticks 50 reach the food to be subsequently ingested, the gyroscope 55 stops outputting the moment.

The configuration of the recommendation system according to the present embodiment has been described above. Next, an operational process of the recommendation system according to the present embodiment will be described.

2-2-3. Operational Process of Recommendation System

In the recommendation system according to this embodiment, the server 40 selects the food to be subsequently ingested based on the image captured by the camera 30 and guides the user 8 by the chopsticks 50. The operational process of the recommendation system according to the present embodiment is the same as the operational process performed by the HMD 1 described above with reference to FIG. 4 and is different in the recommendation process of step S120. More specifically, in the first embodiment, the emphasis image or the inhibitive image is displayed as the recommendation process on the display unit 2 of the HMD 1. In the present embodiment, however, the guidance by the chopsticks 50 is performed. Thus, a recommendation process by the chopsticks 50 of the recommendation system will be described below with reference to FIG. 7.

Figure 7:
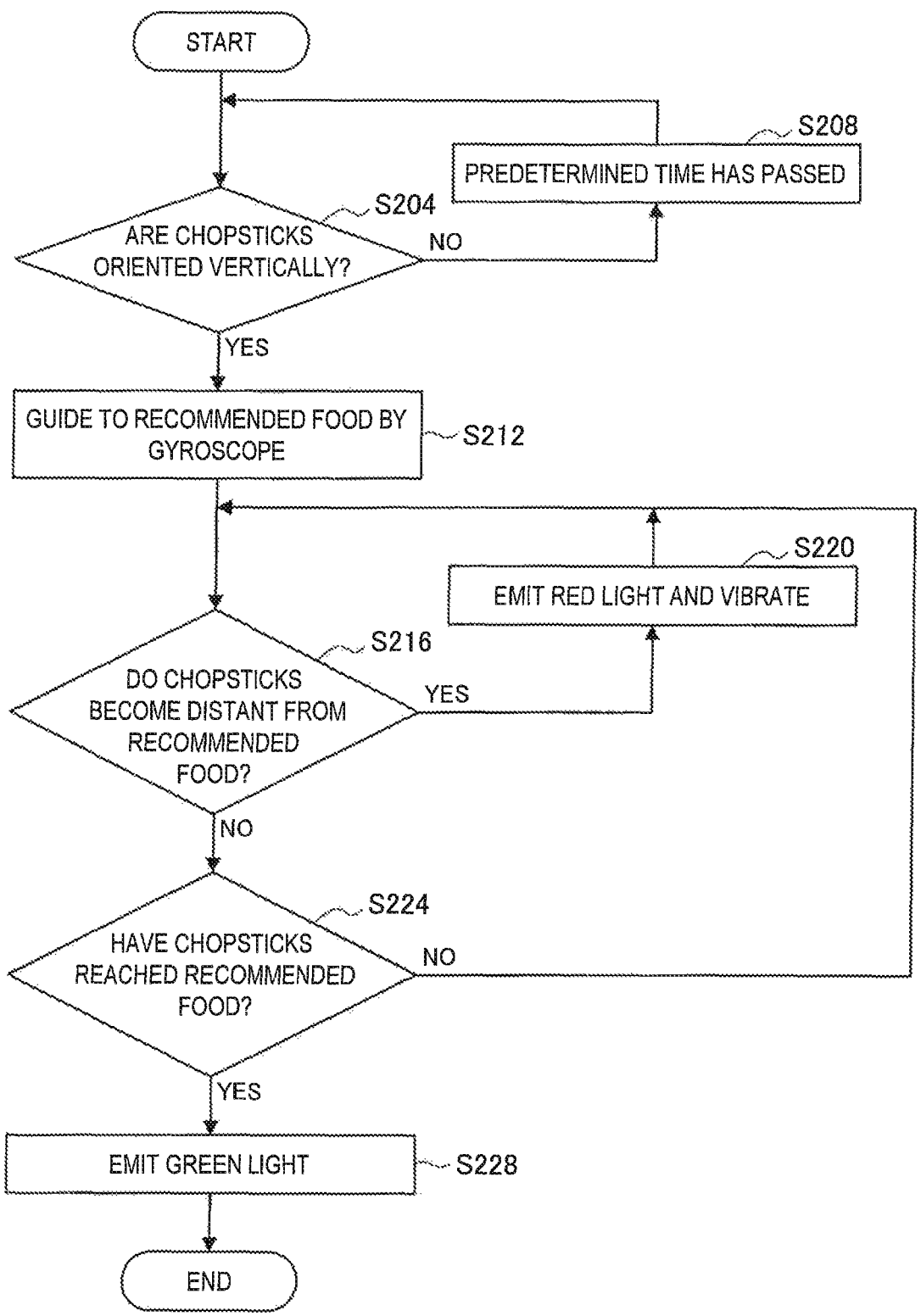
FIG. 7 is a flowchart illustrating a recommendation process of the recommendation system according to the second embodiment.

FIG. 7 is a flowchart illustrating the recommendation process of the recommendation system according to the second embodiment. As illustrated in FIG. 7, in step S204, the control unit 52 of the chopsticks 50 first causes a vertical determination sensor (not illustrated) to determine whether the chopsticks 50 are oriented in the vertical direction.

When the chopsticks 50 are not oriented in the vertical direction (NO in S204), the control unit 52 of the chopsticks 50 stands by until a predetermined time passes in step S208 and the process returns to step S204 again.

When the chopsticks 50 are oriented in the vertical direction (YES in S204), the chopsticks 50 guide the user 8 in the direction of the food recommended by the recommendation unit 13-2 in step S212. Specifically, based on the guidance information received from the server 40, the control unit 52 of the chopsticks 50 controls the gyroscope 55 and causes the gyroscope 55 to output a moment so that the chopsticks 50 are tilted in the direction of the recommended food indicated by the guidance information.

Subsequently, in step S216, the control unit 52 of the chopsticks 50 determines whether the chopsticks 50 become distant from the food recommended by the recommendation unit 13-2. Specifically, based on various kinds of positional information included in the guidance information received from the server 40, the control unit 52 of the chopsticks 50 determines whether the positions of the chopsticks 50 become distant from the position of the food recommended by the recommendation unit 13-2. Furthermore, the server 40 may determine whether the chopsticks 50 become distant from the food recommended by the recommendation unit 13-2 based on the image captured by the camera 30 and transmit the determination result as the guidance information to the chopsticks 50.

When the chopsticks 50 become distant from the food recommended by the recommendation unit 13-2 (YES in S216), the light-emitting unit 54b emits the red light and the vibration unit 53 vibrates in step S220. Thus, the chopsticks 50 can notify the user 8 that the user 8 is ingesting the food in a wrong order. Thereafter, the process returns to step S216 again.

Conversely, when the chopsticks 50 do not become distant from the food recommended by the recommendation unit 13-2 (NO in S216), the control unit 52 of the chopsticks 50 determines whether the chopsticks 50 have reached the food recommended by the recommendation unit 13-2 in step S224. Specifically, based on various kinds of positional information included in the guidance information received from the server 40, the control unit 52 of the chopsticks 50 determines whether the positions of the chopsticks 50 accord with or are in the vicinity of the position of the food recommended by the recommendation unit 13-2. Furthermore, based on the image captured by the camera 30, the server 40 may determine whether the chopsticks 50 have reached the food recommended by the recommendation unit 13-2 and transmit the determination result as guidance information to the chopsticks 50.

When the chopsticks 50 have not reached the food recommended by the recommendation unit 13-2 (NO in S224), the process returns to step S216 again.

Conversely, when the chopsticks 50 have reached the food recommended by the recommendation unit 13-2 (YES in S224), the light-emitting unit 54a emits the green light in step S228. Thus, the chopsticks 50 can notify the user 8 that the user 8 is ingesting the food in the right order.

The operational process of the recommendation system has been described above.

(Supplement)

The example in which the user 8 is guided by the eating utensil gripped by the user 8 has been described above, but the recommendation system according to the present embodiment is not limited to this example. For example, the recommendation system may guide the user 8 using an eating utensil not gripped by the user 8, such as a cup or a plate. For example, the recommendation system may cause a light-emitting unit formed in a plate on which the food to be subsequently ingested is placed to emit light or may cause a plate on which food to be inhibited from being subsequently ingested is placed to vibrate when the user 8 ingests this food. Also, a wristwatch, a wristband, a ring, or the like which the user 8 wears on his or her body may have the function of the chopsticks 50 and guide the user 8 through light emission or vibration. Furthermore, the recommendation system may transmit information indicating the food to be subsequently ingested to an information processing device such as a smartphone or a tablet terminal present in the vicinity of the user 8 and may display the information processing device to display an order of eating.

Also, in the present embodiment, the case in which the selection process is performed by the control unit 10-2 of the server 40 has been described, but the selection process may be performed by the camera 30 or the chopsticks 50. For example, the camera 30 may select the food to be subsequently ingested based on a captured image and wirelessly communicate the guidance information to the chopsticks 50.

Furthermore, the chopsticks 50 may select the food to be subsequently ingested based on a captured image received from the camera 30 and guide the user 8. Also, the server 40, the camera 30, and the chopsticks 50 may separately have the functions of the detection unit 11, the recognition unit 12, the recommendation unit 13-2, and the storage unit 7.

Also, in the present embodiment, the example in which the chopsticks 50 guide the user 8 through the output of the moment by the gyroscope 55 has been described, but the present embodiment is not limited to this example. For example, the chopsticks 50 may perform guidance using a piezoelectric element. Here, the piezoelectric element is an element which has a property in which a voltage is generated when a force is applied and the piezoelectric element is deformed, and conversely the piezoelectric element is deformed when a voltage is added. For example, the chopsticks 50 may perform the guidance in such a manner that the chopsticks 50 are bent to form a shape which is difficult to use when the chopsticks 50 become distant from the recommended food, and the chopsticks 50 form a linear shape which is easy to use when the chopsticks 50 reach the recommended food.

2-2-4. Modification Example

The present modification example is an example in which the food to be subsequently ingested is recommended and the user 8 is guided by a device installed in the vicinity of the user 8. Hereinafter, a recommendation system according to the present modification example will be described with reference to FIG. 8.

FIG. 8 is an explanatory diagram illustrating an overview of a recommendation system according to a modification example. As illustrated in FIG. 8, the recommendation system according to the modification example includes a camera 30, a server 40, a speaker 60, and an illumination device 70. In the recommendation system according to the modification example, the camera 30 transmits an image obtained when the camera 30 images eating of the user 8 to the server 40, the server 40 selects the food to be subsequently ingested by the user 8, and the speaker 60 and the illumination device 70 guide the user 8 to the food selected by the server 40.

In the example illustrated in FIG. 8, the recommendation system causes the illumination device 70 to light up the salad 21 such that the user first ingests the salad 21 containing many vegetables under the assumption that the user first ingests vegetables for the purpose of diabetes countermeasures. Simultaneously, the recommendation system recommends the salad 21 to the user 8 by outputting an audio from the speaker 60 to guide the user so that the user ingests the salad 21.

Thus, the recommendation system can recommend the food to be subsequently ingested to the user 8, using not only an eating utensil gripped by the user 8 but also a device installed in the vicinity of the user 8.

The modification example has been described above.

3. CONCLUSION

As described above, the information processing device (the HMD 1 and the server 40) according to the embodiments of the present disclosure can promote health of the user 8 by performing navigation in an order of eating in real time. In particular, the information processing device according to the embodiments of the present disclosure can perform navigation so that the user ingests food in orders satisfying various purposes such as diabetes countermeasures, hyperlipemia countermeasures, obesity countermeasures, education, enjoyment, a comfortable meal, and adherence to guidance of a doctor. Therefore, the information processing device according to the embodiments of the present disclosure can support dietary life to promote the health or enjoyment of meals for the user 8 from various viewpoints.

The HMD 1 according to the first embodiment displays the emphasis image and the inhibitive image so that the user 8 can ingest food in the recommended order without being given stress. Therefore, the HMD 1 can support healthy dietary life without lowering enjoyment of the meal by the user 8.

The server 40 according to the second embodiment can guide the user 8 so that the user 8 can ingest food in the recommended order using the chopsticks 50, another eating utensil, or a device installed in the vicinity of the user 8.

The preferred embodiments of the present disclosure have been described in detail above with reference to the appended drawings, but the technical scope of the present disclosure is not limited to the examples. It should be understood by those skilled in the technical fields of the present disclosure that various modifications or corrections may be made within the technical spirit and essence described in the claims and are, of course, construed to pertain to the technical scope of the present disclosure.

Also, a computer program can be created to cause hardware such as a CPU, a ROM, and a RAM included in the information processing device to have the equivalent functions of the configuration of the HMD 1 or the server 40 described above. Also, a storage medium storing the computer program therein is also provided.

Additionally, the present technology may also be configured as below.

(1)
An information processing device including:
a detection unit configured to detect a plurality of pieces of food which are eating targets from an image obtained by imaging eating of a user, and
a recommendation unit configured to recommend at least the food to be subsequently ingested in real time among the plurality of pieces of food so that the user ingests the plurality of pieces of food detected by the detection unit in an order satisfying a predetermined purpose.

(2)
The information processing device according to (1), wherein the recommendation unit generates an emphasis image showing the food to be subsequently ingested in an emphatic manner and causes a display unit to display the emphasis image.

(3)
The information processing device according to (1) or (2), wherein the recommendation unit generates an inhibitive image showing the food to be inhibited from being subsequently ingested in an inhibitive manner and causes a display unit to display the inhibitive image.

(4)
The information processing device according to any one of (1) to (3), further including:
an accumulation unit configured to accumulate a history of past eating of the user,
wherein the recommendation unit recommends at least the food to be subsequently ingested further based on the history accumulated by the accumulation unit.

(5)
The information processing device according to any one of (1) to (4), further including:
a recognition unit configured to recognize an eating situation of the user from the image obtained by imaging the eating of the user,
wherein the recommendation unit recommends at least the food to be subsequently ingested further based on the situation recognized by the recognition unit.
(6)
The information processing device according to any one of (1) to (5), further including:
a transmission unit configured to transmit guidance information for guiding the user to the food recommended by the recommendation unit to an eating utensil having a function of guiding the user based on received information.
(7)
The information processing device according to (2), wherein the emphasis image is an image beautifying an outer appearance of the food.
(8)
The information processing device according to (3), wherein the inhibitive image is an image degrading an outer appearance of the food.
(9)
The information processing device according to (3), wherein the inhibitive image is an image screening the food from the user.
(10)
The information processing device according to any one of (1) to (9), wherein the order satisfying the predetermined purpose is an order of suppressing an increase in a blood-sugar level of the user.
(11)
A non-transitory computer-readable storage medium having a program stored therein, the program causing a computer to execute:
detecting a plurality of pieces of food which are eating targets from an image obtained by imaging eating of a user, and
recommending at least the food to be subsequently ingested in real time among the plurality of pieces of food so that the user ingests the plurality of pieces of food detected by the user in an order satisfying a predetermined purpose.

What is claimed is:
1. An information processing device comprising:
a detection unit configured to detect a plurality of eating targets from an image obtained by imaging the eating targets and eating utensil of a user, wherein each detected eating target of the plurality of eating targets comprises a type distinct from other detected eating targets of the plurality of eating targets in the obtained image; and
a recommendation unit configured to recommend what particular eating target of the detected plurality of eating targets the user should ingest next in time, according to an order of ingesting the detected plurality of eating targets satisfying a predetermined purpose and based on a determination of previously ingested eating targets of the detected plurality of eating targets,
wherein the recommendation unit is further configured to generate guidance information based on a real-time recognition of whether the detected plurality of eating targets have been ingested in the recommended order of ingesting,
wherein whether the detected plurality of eating targets have been ingested in the recommended order of ingesting is recognized based on positional information of the eating utensil,
wherein the generated guidance information is presented to the user in an overlapping manner by a head mounted display (HMD) configured to be worn by the user with at least one eating target of the plurality of eating targets in order to recommend the particular eating target while the user views the plurality of eating targets, and
wherein the detection unit and the recommendation unit are each implemented via at least one processor.

2. The information processing device according to claim 1, wherein the recommendation unit generates an emphasis image showing the particular eating target of the plurality of eating targets to be ingested next in time in an emphatic manner and causes a display unit to display the emphasis image.

3. The information processing device according to claim 1, wherein the recommendation unit generates an inhibitive image showing eating targets of the detected plurality of eating targets to be inhibited from being ingested next in time in an inhibitive manner and causes a display unit to display the inhibitive image.

4. The information processing device according to claim 1, further comprising:
an accumulation unit configured to accumulate a history of the previously ingested eating targets of the user,
wherein the recommendation unit recommends at least the particular eating target of the plurality of eating targets to be ingested next in time further based on the history accumulated by the accumulation unit, and
wherein the accumulation unit is implemented via at least one processor.

5. The information processing device according to claim 1, further comprising:
a recognition unit configured to recognize an eating situation of the user from the image obtained by imaging the eating targets of the user,
wherein the recommendation unit recommends at least the particular eating target of the detected plurality of eating targets to be ingested next in time further based on the situation recognized by the recognition unit, and
wherein the recognition unit is implemented via at least one processor.

6. The information processing device according to claim 1, further comprising:
a transmission unit configured to transmit guidance information for guiding the user to each particular eating target of the detected plurality of eating targets recommended by the recommendation unit to an eating utensil having a function of guiding the user based on received information regarding the recommended order of the detected plurality of eating targets,
wherein the transmission unit is implemented via at least one processor.

7. The information processing device according to claim 2, wherein the emphasis image is an image beautifying an outer appearance of the particular eating target of the detected plurality of eating targets.

8. The information processing device according to claim 3, wherein the inhibitive image is an image degrading an outer appearance of the eating targets of the detected plurality of eating targets to be inhibited.

9. The information processing device according to claim 3, wherein the inhibitive image is an image screening the eating targets of the detected plurality of eating targets to be inhibited from the user.

10. The information processing device according to claim 1, wherein the order satisfying the predetermined purpose is an order of the detected plurality of eating targets suppressing an increase in a blood-sugar level of the user.

11. A non-transitory computer-readable storage medium having a program stored therein, which when executed by an information processing device of a computer, causes the computer to execute a method, the method comprising:
    detecting a plurality of eating targets from an image obtained by imaging the eating targets and eating utensil of a user, wherein each detected eating target of the plurality of eating targets comprises a type distinct from each other detected eating target of the plurality of eating targets in the obtained image; and
    recommending what particular eating target of the detected plurality of eating targets the user should ingest next in time, according to an order of ingesting the detected plurality of eating targets satisfying a predetermined purpose and based on a determination of previously ingested eating targets of the detected plurality of eating targets,
    wherein the recommending further comprises generating guidance information based on a real-time recognition of whether the detected plurality of eating targets have been ingested in the recommended order of ingesting, and
    wherein whether the detected plurality of eating targets have been ingested in the recommended order of ingesting is recognized based on positional information of eating utensil,
    wherein the generated guidance information is presented to the user in an overlapping manner by a head mounted display (HMD) configured to be worn by the user with at least one eating target of the plurality of eating targets in order to recommend the particular eating target while the user views the plurality of eating targets.

12. The information processing device according to claim 1, wherein the detected plurality of eating targets comprise a plurality of pieces of food.

13. The non-transitory computer-readable storage medium according to claim 11, wherein the detected plurality of eating targets comprise a plurality of pieces of food.

* * * * *